United States Patent [19]

Adler et al.

[11] Patent Number: 4,574,637

[45] Date of Patent: Mar. 11, 1986

[54] METHOD FOR MEASURING SURFACE AND NEAR SURFACE PROPERTIES OF MATERIALS

[76] Inventors: Laszlo Adler, 2850 Canterbury La., Upper Arlington, Ohio 43221; Dale W. Fitting, P.O. Box 013, 1405 Ann, Ann Arbor, Mich. 48109; Michel de Billy, 38 Avenue Emile Zola, Paris 75015, France

[21] Appl. No.: 637,400

[22] Filed: Aug. 3, 1984

[51] Int. Cl.$^4$ ............................................. G01N 29/00
[52] U.S. Cl. ...................................... 73/629; 73/599; 73/620; 73/633
[58] Field of Search ................. 73/573, 588, 606, 620, 73/629, 633, 599

[56] References Cited

U.S. PATENT DOCUMENTS

| | | | |
|---|---|---|---|
| 3,512,400 | 5/1970 | Lynnworth | 73/629 |
| 3,938,371 | 2/1976 | Dini | 73/629 |
| 4,307,614 | 12/1981 | Tittman et al. | 73/629 |
| 4,457,174 | 7/1984 | Bar-Cohen et al. | 73/629 |

FOREIGN PATENT DOCUMENTS 2429430  1/1980  France ................................. 73/629

OTHER PUBLICATIONS

"Acoustic-Backscattering Imaging of Subcritical Flaws in Composites", Bar-Cohen et al., technical paper, Nov. 81.
Ultrasonic Leaky Waves in the Presence of a Thin Layer; A. H. Nayfeh, D. E. Chimenti, Laszlo Adler, and R. L. Crane; Feb. 23, 1981; pp. 4985-4994.
Effective Case Depth: Uncertainties in Measurement; A. J. Berry et al.; Nov. 7, 1968; pp. 373-385.
Use of Ultrasonic Rayleigh Waves for the Measurement of Applied Biaxial Surface Stresses in Aluminum 2024-T351 Alloy; K. Jassby et al.; Feb. 1982; pp. 198-205.
Use of Ultrasonic Goniometer to Measure Depth of Case Hardening (The Corner Reflection Method); W. Weston-Bartholomew; 1979; pp. 111-123.
Parameters Affecting Backscattered Ultrasonic Leaky Rayleigh Waves from Liquid-Solid Interfaces: Michel de Billy et al.; May 31, 1982; pp. 1018-1020.
Magnetic and Electromagnetic Methods; A. M. Gorki; Feb. 1979; pp. 93-96.
Rayleigh-Wave Propagation in Media Exhibiting Elastic Property Gradients; B. G. Martin; pp. 311-314.
Deducing Subsurface Property Gradients from Surface Wave Dispersion Data; John Richardson; pp. 769-790.
Estimation of Surface Layer Structure from Rayleigh Wave Dispersion: Dense Data Case; J. M. Richardson; Apr. 7, 1976; pp. 498-512.
Ultrasonic Dispersion; T. L. Szabo; pp. 163-172.
Residual Stress Measurements from Surface Wave Velocity Dispersion; Thomas Szabo; pp. 749-767.
Nondestructive Subsurface Gradient Determination; Thomas L. Szabo; pp. 565-567.
Obtaining Subsurface Profiles from Surface-Acoustic-Wave Velocity Dispersion; T. L. Szabo; Apr. 4, 1975; pp. 1448-1454.
Deducing Subsurface Property Gradients from Wave Dispersion Data; John M. Richardson et al.; 1975; pp. 488-491.
Estimation of Surface-Layer Structure from Rayleigh-Wave Dispersion, III., Sparse Data Case—Interpretation of Experimental Data; B. R. Tittman et al.; Apr. 25, 1978; pp. 5242-5249.

(List continued on next page.)

Primary Examiner—Howard A. Birmiel
Attorney, Agent, or Firm—Sidney W. Millard

[57] ABSTRACT

The properties of the surface layer of a material are measured by a technique which employs the transmission of ultrasonic waves from varying angles of incidence into a specimen, from a transducer at a point spaced from the specimen. The backscattered waves are detected and evaluated from the varying angles to detect the local maximum intensity, from which the corresponding properties of the material are determined.

10 Claims, 2 Drawing Figures

OTHER PUBLICATIONS

Estimation of Surface Layer Structure from Rayleigh Wave Dispersion II., Sparse-Data Case—Analytical Theory; J. M. Richardson et al.; Aug. 4, 1977; pp. 5111-5121.

Ultrasonic Bounded Beam Reflection Effects at a Liquid-Anisotropic-Solid Interface; Thomas J. Plona, Dec. 1975; pp. 1773-1775.

Rayleigh Wave Dispersion in the Cold-Worked Layer of Used Railroad Rail; Don E. Bray; Sep. 1978; pp. 845-851.

Dumping of Rayleigh Waves in a Elastic Layer Above a Half-Space; N. N. Egorov; Jul.-Sep. 1961; pp. 378-380.

The Effect of Near-Surface Metallic-Property Gradients on Ultrasonic Critical-Angle Reflectivity; B. G. Martin; Jan. 1980; pp. 92-96.

METHOD FOR MEASURING SURFACE AND NEAR SURFACE PROPERTIES OF MATERIALS

This invention was made with Government support under Grant No. ISI-8018104 awarded by the National Science Foundation. The Government has certain rights in this invention.

BACKGROUND OF THE INVENTION

This invention relates to a method for measuring surface and near surface mechanical properties of materials. More particularly, the invention relates to an ultrasonic method for measuring the properties of the surface layer of a specimen in which the surface layer has at least one physical property the value of which differs from the same physical property of the subsurface layer of the specimen.

One of the most difficult objectives in the nondestructive testing of materials is measurement of the properties of a thin surface layer, the properties of which differ from the corresponding properties in the subsurface layer or bulk material lying within a specimen. For example, Berry and Mulhearn, Effective Case Depth: Uncertainties in Measurement, Metallography, 1, 373-385 (1969) discuss the sources of uncertainty in the measurement of effective case hardening depths of surface hardening steel by the traditional destructive method of cutting a section through the case hardened steel and measuring the hardness of various points on the cross-section thus exposed using a loaded, pointed probe. Case-hardening depths have also been measured using eddy current and coercive force measurements (see, for example, Metal Progress, August, 1971, page 55); but such measurements involve the use of complicated and expensive equipment and only yield an average value of case hardening depths over the whole specimen tested. Attempts have also been made to measure the depths of surface layers using Rayleigh or surface waves propagated through the surface layer. For example, Jaspy and Saltoun, Use of Ultrasonic Rayleigh Waves for the Measurement of Applied Biaxial Surface Stresses in Aluminum 2024-T351 Alloy, Materials Evaluation 40, 1982 (February, 1982) describes a time-of-flight measurement technique in which a transmitting ultrasonic transducer is coupled to the surface of a specimen via a plastic wedge and causes propagation of Rayleigh waves through the surface layer of the specimen. Two steel wedges are in contact with the surface of the specimen at points spaced from one another and from the plastic wedge, and pick-up transducers are mounted on the upper ends of either of the wedges. The velocity of the Rayleigh waves through the surface layer, and hence information on the surface layer, is determined by the time-of-flight of the Rayleigh waves between the points at which the two steel wedges contact the surface of the specimen. Since this is a time-of-flight measurement method, it only yields an average value for the properties of the surface layer in the distance between the two steel wedges, a distance which in the experimental apparatus needs to be about 11 millimeters, a distance which may encompass considerable variation of the surface layer in some specimens. Moreover, not only does the method require the use of three transducers and appropriate associated electronics, but it is only really well suited to measurements on specimens having a flat or only gently curving surface; in many practical applications, it would be difficult or physically impossible to engage the transmitting transducer, the plastic wedge and the two steel wedges in position on the specimen.

Two other techniques for measurement of properties of surface layers by means of Rayleigh waves are disclosed in Weston-Bartholomew, Use of the Ultrasonic Goniometer to Measure Depth of Case Hardening (The Corner Reflection Method). In the first of these two methods, a transmitting ultrasonic transducer immersed in a water bath is used to transmit an ultrasonic beam, which impinges upon the surface of a specimen also immersed in the water bath. The impingement of the ultrasonic beam upon the surface produces a reflected ultrasonic beam (in the usual sense of a beam lying at the same angle to the perpendicular to the surface of the specimen, but on the opposed side of this perpendicular), and this reflected beam is detected by means of a second transducer immersed in the water bath. Although this method has the advantage that, since only the properties of the specimen at the point of impact of the beam thereon affect the measurements taken, by the use of relatively narrow beams the method can effectively measure the properties of the surface layer at a single point, the method does require the use of two separate transducers. Furthermore, it is normally necessary to vary the angle of incidence (and thus also the angle of the reflected beam) to the surface of the specimen in order to observe the local maximum of intensity of the reflected beam which occurs at the Rayleigh angle of the specimen. In order to achieve the necessary variation in the angles of incidence of reflection at least two of the three components (the two transducers and the specimen itself) must be mounted for rotation about the same axis which must pass through the surface of the specimen at the point at which the measurements are being taken. In view of the relatively small changes in Rayleigh angle which must be measured in practice (of the order of 0.1°), providing such accurate rotation of at least two components while maintaining proper alignment presents formidable practical difficulties.

In the second method disclosed in Weston-Bartholomew, only a single transducer is used, but a reflector block is mounted on the specimen so that an ultrasonic pulse from the transducer will strike the surface of the specimen, thereby generating a reflected beam which strikes a surface of the reflector block lying perpendicular to the surface of the specimen. The impingement of the reflected beam upon the surface of the reflector block produces a second reflected beam travelling in the opposite direction to the incident beam, so that this second reflected beam can be detected by the transducer, which is of course operated in the pulse-echo mode. Although this second method does require only a single transducer and requires that only one of the transducer and specimen be rotatable, thus reducing many of the alignment problems in the first Weston-Bartholomew method, it does have the disadvantage of requiring very careful alignment of the surface of the reflector block perpendicular to the surface of the specimen, and the time taken for alignment with the necessary degree of precision renders this second method impracticable for use in a routine production line industrial situation. More importantly, since the second method requires the presence of a reflector block of some considerable size immediately adjacent, if not actually attached to, the surface of the specimen, this second method cannot be used to investigate small sections of a component of complex form, for example a toothed gear wheel, because in such situations there would simply be no room for the reflector block.

There is thus a need for a method of measuring the properties of a surface layer of a specimen which uses simple apparatus, which is suitable for use in an industrial production line situation, which is nondestructive and which enables properties of small parts of the surface layer to be measured even on specimens having a complex form. This invention seeks to provide such a method.

SUMMARY OF THE INVENTION

This invention provides a method of measuring the properties of the surface layer of a specimen having both the surface layer and a subsurface layer, the surface layer having at least one physical property the value of which differs from the same physical property in the subsurface layer. In the instant method, an ultrasonic transducer is disposed at the point spaced from the specimen and is caused to generate a pulse of ultrasound which impinges upon the surface layer of the specimen. The impingement of the pulse of ultrasound upon the surface layer of the specimen generates a backscattered pulse which is detected by means of the transducer. The generation of the pulse of ultrasound and detection of the backscattered pulse from the specimen are repeated while the angle of incidence of the pulse upon the surface of the specimen is varied and the local maximum of intensity of the backscattered pulse which occurs when the angle of incidence is approximately equal to The Rayleigh angle of the surface layer is detected. The angle of incidence at this local maximum of intensity is then measured.

DETAILED DESCRIPTION OF THE INVENTION

Figure 1:
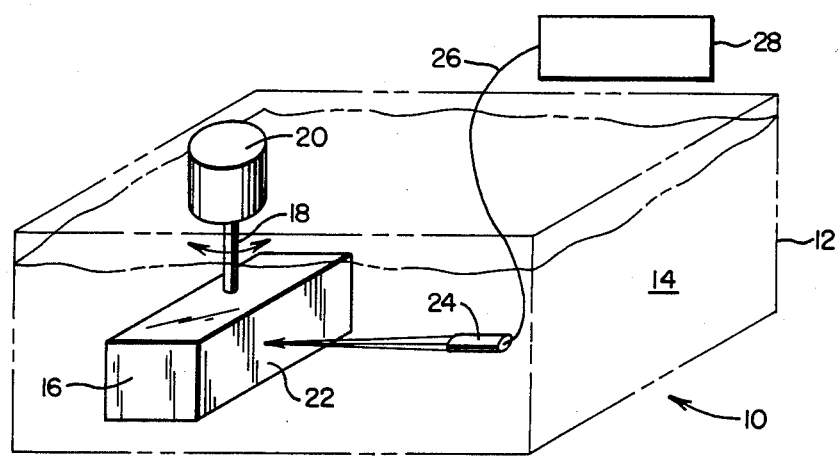
FIG. 1 is a schematic view of a first apparatus used in the instant method.

From the foregoing Summary of the Invention, it will be seen that the instant method relies upon the fact that impingement of as pulse of ultrasound upon the surface layer of the specimen causes generation of a backscattered pulse which can be detected by the same transducer used to generate the incident pulse. The presence of this backscattered pulse has previously been known; see de Billy et al., Parameters affecting backscattered ultrasonic leaky-Rayleigh waves from liquid-solid interfaces, J. Acoust Soc. Am., 72, 1018–1020 (1982) and references cited therein. This paper by de Billy et al. shows that the amplitude of the backscattered pulse is strongly dependent on the angle of incidence, a strong local maximum appearing when the angle of incidence is approximately equal to the Rayleigh angle for the interface between a specimen and the medium surrounding the specimen. However, the de Billy et al. paper does not report any experiments with heterogeneous specimens having a surface layer differing in properties from a subsurface layer, and since the appearance of the backscattered pulsed is not predicted by any available theoretical model, theoretical investigations of variations in the backscattered pulse with variations in the specimen being investigated have been impossible. Accordingly, hitherto it has not been known that useful information concerning the surface layer of a heterogeneous specimen having a surface layer differing in properties form its subsurface layer could be obtained by means of such backscattered pulses.

In the instant method, desirably the transducer and at least the portion of the specimen on which the pulse impinges are immersed in a liquid so that the pulse and the backscattered pulse travel through the liquid. The liquid, which is conveniently water, acts as a coupling medium ensuring efficient transmission of the pulse from the transducer to the specimen, and of the backscattered pulse from the specimen back to the transducer. Moreover, since the Rayleigh angle, R, is given by:

$$\sin R = V_1/V_s$$

where $V_1$ and $V_s$ are the velocities of the ultrasonic wave in the liquid and the solid specimen respectively ($V_s$ is the effective wave speed in the specimen, which in the instant method effectively means in the appropriate surface layer, as discussed in more detail below). Since the wave speed in liquid is higher than the wave speed in air or gases, use of the liquid increases the Rayleigh angle, so making the measurement of this angle more accurate. The instant method requires that the angle of incidence of the ultrasonic pulse be varied so that the local maximum of intensity which occurs at the Rayleigh angle can be detected. Because the instant method makes use of the backscattered pulse and needs only a single transducer, only one of the specimen and transducer need be pivotable to allow variation in the angle of incidence. Furthermore, in contrast to the second Weston-Bartholomew method described above, no accurate alignment of any other component with the surface of the specimen or with the transducer is required. Thus, the instant method greatly reduces the alignment problems associated with prior art ultrasonic methods for the investigation of surface layers. Either the specimen or the transducer may be made pivotable relative to the other component. Thus, the specimen may be mounted upon a pivotable specimen support with a part of the surface layer disposed substantially on the axis of pivoting of this support and the pulse of ultrasound arranged to impinge upon the part of the surface layer disposed substantially on the pivoting axis. Alternatively, the specimen may be held in a fixed position and the transducer mounted on a pivotal support arranged so that the transducer can be pivoted about a point lying on the surface layer of the specimen, the transducer being arranged so that the pulse of ultrasound which it generates impinges upon this point.

From experiments using specimens carburized to differing depths, it has been found that the Rayleigh angle detected by means of the backscattered pulse in the instant method depends upon the relationship of the frequency of the ultrasonic pulse to the depth of the surface layer. Accordingly, it is advantageous, in the instant method, to carry out the instant method using at least two different frequencies of ultrasound and measure the angle of incidence at the local maximum of intensity separately for each of the frequencies used. As will be apparent to those skilled in the art, variation in the frequency of the incident ultrasonic beam in the instant method can be achieved by changing the transducer and/or the mode of excitation thereof so that only a single frequency of ultrasonic pulse is generated at any one time, with separate experiments being performed at each frequency to be used. Alternatively, it may be possible to use an ultrasonic transducer which generates a variety of frequencies at one time and then to carry out more sophisticated analysis to identify the Rayleigh angle for a variety of frequencies within the range generated by the transducer. Given that the surface layers which it is desired to measure in practice are usually of the order of about 1 millimeter thick, the range of ultrasonic frequencies used in the instant method will typically be from about 0.5 to about 10 MHz.

As already mentioned, the variation of Rayleigh angle with ultrasonic frequency has been examined using specimens carburized to varying depths. When the Rayleigh angles determined are plotted against depth of hardness, and the Rayleigh wave speed (calculated from the Rayleigh angle) is plotted against the product of frequency of incident ultrasonic pulse and depths of surface layer, the curves exhibit a characteristic shape. For surface layer depths less than about 0.8 times that Rayleigh wavelength, the Rayleigh wave speed decreases almost linearly with increasing values of frequency times depth. The minimum value of Rayleigh wave speed is reached at a frequency times depth value of about 0.8 times the Rayleigh wavelength. Above this value, the Rayleigh wave speed again increases, although the rate of increase soon begins to slow and a plateau in the Rayleigh wave speed is achieved at a frequency times depth measurement of approximately 1.7 times the Rayleigh wavelength. It is believed (although the invention is in no way limited by this belief) that the reason for the variations in Rayleigh angle with depth of the surface layer and frequency of the incident ultrasonic pulse are as follows. Lower frequency, long wavelength Rayleigh waves tend to penetrate more deeply into the surface of the material than high frequency waves. For thicknesses of surface layer less than 0.8 times the Rayleigh wavelength, the Rayleigh wave has a penetration depth exceeding the depth of the surface layer so that the wave speed is thus affected by the properties of the subsurface layer as well as the surface layer. As the frequency of the incident ultrasonic beam is raised for any given depth of surface layer, the propagation of the Rayleigh wave is increasingly confined to the surface layer and penetration into the subsurface layer is reduced. For Rayleigh wavelengths approximately equal to the thickness of the surface layer, the effect on dispersion is maximized. As the frequency increases still further, the penetration of the Rayleigh wave decreases further and propagation only occurs within a portion of the surface layer.

Thus, the change in the Rayleigh angles with frequency measured by the instant method may be used to determine the thickness of the surface layer of a specimen. Although we have not yet achieved this, it is believed that inversion methods, such as those described in:

Auld, Acoustic Fields and Waves in Solids, Volume II (Wiley, New York, 1973); and
Tittmann and Tompson, Proceedings of the 5th Symposium on Nondestructive Evaluation, 20–28 (San Antonio, Tex., 1973)

may be used to explore the variation of properties within the surface layer as well as the depth of this layer. Such methods may be especially useful for exploring the variation in hardness within specimens, for example case hardened specimens, in which the surface layer is of a different hardness from the subsurface layer. However, the instant method is not of course restricted to specimens displaying such a variation in hardness. For example, the instant method may be used in specimens where the surface layer differs in physical properties from the subsurface layer as a result of heat treatment, or in which the surface layer differs from the subsurface layer in the amount of residual stress therein.

FIG. 1 shows schematically a first apparatus of the invention (generally designated 10) in which the transducer is held fixed and the specimen rotates. The apparatus shown in FIG. 1 comprises a cuboidal tank 12 open at its upper face and almost filled with water 14. A specimen 16 is rotatably mounted within the water 14, the specimen 16 being mounted on a shaft 18 pivotable by means of an electric motor 20. The shaft 18 is arranged very close to the front surface 22 of the specimen 16, so that the axis of rotation almost passes through this surface. An ultrasonic transducer 24 is fixedly mounted within the water 14 by means of a suitable support (not shown) and is connected by means of conductors 26 to associated electronic apparatus indicated schematically at 28. This electronic apparatus 28 may be any of a variety of commercially available units capable of operating the transducer 24 in the pulse-echo mode. For obvious reasons, the electronic apparatus 28 should have high gain and low noise. It may comprise a toneburst pulser with a broadband or tuned receiving amplifier, or a broadband pulser with provisions for quantitative spectrum analysis of the backscattered ultrasonic pulse. It has been found that the Matec Pulse Modulator Detector Model 6600 (commercially available from Matec, Warwick, R.I.) gives satisfactory results. The transducer 24 is arranged so that it transmits pulses of ultrasound towards, and receives backscattered pulses from, the surface 22 of the specimen 16 lying adjacent the shaft 18.

Figure 2:
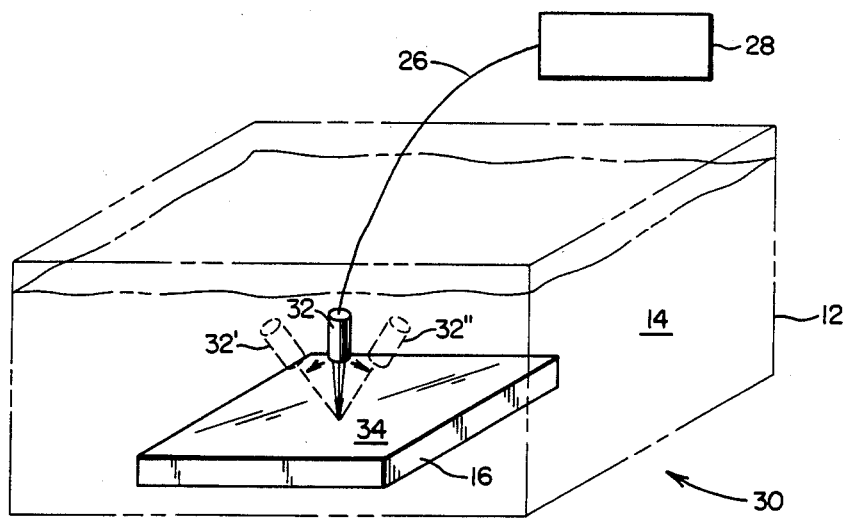
FIG. 2 is a schematic view of a second apparatus used in the instant method.

The second instant apparatus (generally designated 30) shown in FIG. 2 is generally similar to the apparatus 10 shown in FIG. 1 except that the second instant apparatus uses a fixed specimen and a pivotable transducer. The second apparatus 30 comprises a tank 12 and water 14 identical to the corresponding parts of the first apparatus 10. However, in the apparatus 30 the specimen has the form of a flat plate fixedly mounted by means of a support (not shown) adjacent the bottom of the tank 12. A transducer 32, connected by conductors 26 to electronics 28 in the same manner as the transducer 24 shown in FIG. 1, is pivotally mounted by means of a pivoting support (not shown) within the water 14 in the tank 12 so that the transducer 32 can pivot about a point on the upper surface 34 of the specimen 16, as indicated by the varying transducer positions 32' and 32" shown in FIG. 2.

In the simplest form of the apparatus shown in FIGS. 1 and 2, the specimen 16 shown in FIG. 1 or the transducer 32 shown in FIG. 2 is rotated and separate readings of the intensity of the backscattered beam at various angles of incidence are measured and plotted graphically to locate the angle of incidence at which the local maximum of intensity of backscattered radiation corresponding to the Rayleigh angle occurs. However, as those skilled in the art will be aware, the necessary plotting of the variation of intensity of the backscattered radiation with angle of incidence readily lends itself to automation to allow the plotting to be done electronically, and such automation is of course highly desirable in any form of apparatus intended for use in an industrial environment by relatively unskilled personnel. More specifically, automation of the determination of backscattered intensity with rotation angle is readily achieved by providing the pivotable mounting of the specimen 16 or the transducer 32 with a rotation encoder and feeding the angle signals produced by such a rotational encoder to an electronic data processor, together with signals from the electronic apparatus showing the corresponding values of intensity of the backscattered radiation. The rotation and intensity signals can then be collated and plotted electronically in a manner which will be familiar to those skilled in the art.

It will be apparent to those skilled in the art that numerous changes and modifications can be made in the preferred embodiments of the invention described above without departing from the scope of the invention. Accordingly, the whole of the foregoing description is to be construed in an illustrative and not in a limitative sense, the scope of the invention being defined solely by the appended claims.

We claim:

1. A method of measuring the properties of the surface layer of a specimen having said surface layer and a subsurface layer, said surface layer having at least one physical property the value of which differs from the same physical property of said subsurface layer, which method comprises:
   a. disposing an ultrasonic transducer at a point spaced from said specimen;
   b. causing said transducer to generate a pulse of ultrasound which impinges upon said surface layer of said specimen;
   c. detecting, by means of said transducer, the backscattered pulse produced by said impingement of said pulse upon said surface layer;
   d. repeating the steps (b) and (c) after varying the angle of incidence of the pulse of ultrasound, and detecting the local maximum of intensity of said backscattered pulse which occurs when said angle of incidence is approximately equal to the Rayleigh angle of said surface layer; and
   e. measuring said angle of incidence at said local maximum of intensity.

2. A method according to claim 1 wherein said transducer and at least the portion of said specimen on which said pulse impinges are immersed in a liquid, so that said pulse and said backscattered pulse travel through said liquid.

3. A method according to claim 1 wherein said specimen is mounted upon a pivotable specimen support with a part of said surface layer disposed substantially on the axis of pivoting of said specimen support, and wherein said pulse of ultrasound is arranged to impinge upon said part of said surface layer disposed substantially on said axis.

4. A method according to claim 1 wherein said specimen is held in a fixed position and said transducer is mounted on a pivotable support arranged so that said transducer can be pivoted about a point lying on said surface layer of said specimen, said transducer being arranged so that said pulse of ultrasound generated by said transducer impinges upon said point.

5. A method according to claim 1 wherein said steps (b) to (e) are carried out using at least two different frequencies of said ultrasound, said angle of incidence at said local maximum of intensity being measured separately for each of said frequencies.

6. A method according to claim 1 wherein the frequency of said ultrasound is in the range of about 0.5 to about 10 MHz.

7. A method according to claim 1 wherein said surface layer is of a different hardness from said subsurface layer and wherein said method is used to determine the depth of said subsurface layer.

8. A method according to claim 7 wherein said steps (b) to (e) are carried out using a plurality of different frequencies of said ultrasound, said angle of incidence at said local maximum of intensity being measured separately for each of said frequencies, thereby enabling the variation of hardness with depth of said specimen to be determined from the dispersion of said angles of incidence with said frequencies of said ultrasound.

9. A method according to claim 1 wherein said surface layer differs from said subsurface layer as a result of heat treatment.

10. A method according to claim 1 wherein said surface layer differs from said subsurface layer in the amount of residual stress therein.

* * * * *

UNITED STATES PATENT AND TRADEMARK OFFICE
CERTIFICATE OF CORRECTION

PATENT NO. : 4,574,637
DATED : March 11, 1986
INVENTOR(S) : Laszlo Adler et al.

It is certified that error appears in the above-identified patent and that said Letters Patent is hereby corrected as shown below:

On the title page insert:

-- [73] Assignee: The Ohio State University,

Columbus, Ohio --.

Signed and Sealed this

Second Day of September 1986

[SEAL]

Attest:

DONALD J. QUIGG

Attesting Officer     Commissioner of Patents and Trademarks